(12) United States Patent
Kim et al.

(10) Patent No.: US 12,156,794 B2
(45) Date of Patent: Dec. 3, 2024

(54) PANTS FOR URINE OR FECES AND METHOD OF DISPOSING OF URINE AND FECES

(71) Applicant: Who Young Kim, Icheon-si (KR)

(72) Inventors: Who Young Kim, Icheon-si (KR); Yoon Ho Kim, Cheongju-si (KR); Sang Zoon Buyn, Daejeon (KR); Tae Woong Kwon, Seoul (KR); Soon Jae Im, Seoul (KR)

(73) Assignee: WHO YOUNG KIM, Icheon-si (KR)

( * ) Notice: Subject to any disclaimer, the term of this patent is extended or adjusted under 35 U.S.C. 154(b) by 558 days.

(21) Appl. No.: 17/491,805

(22) Filed: Oct. 1, 2021

(65) Prior Publication Data

US 2022/0023109 A1 Jan. 27, 2022

Related U.S. Application Data

(63) Continuation of application No. PCT/KR2019/006635, filed on Jun. 3, 2019.

(30) Foreign Application Priority Data

Apr. 3, 2019 (KR) .................. 10-2019-0039154
May 21, 2019 (KR) .................. 10-2019-0059408

(51) Int. Cl.
*A61F 13/496* (2006.01)
*A61F 13/495* (2006.01)

(52) U.S. Cl.
CPC .......... *A61F 13/496* (2013.01); *A61F 13/495* (2013.01)

(58) Field of Classification Search
CPC ........ A61F 13/496; A61F 13/495; A61F 5/44; A61F 5/442; A61F 5/451; A61F 5/4408;
(Continued)

(56) References Cited

U.S. PATENT DOCUMENTS

2002/0010446 A1 1/2002 Maimets
2008/0108964 A1* 5/2008 Edwall .................. A61F 13/496
604/385.24
2008/0262458 A1 10/2008 Winqvist

FOREIGN PATENT DOCUMENTS

EP 2255766 A1 12/2010
JP 1986-137557 A 6/1986
(Continued)

OTHER PUBLICATIONS

Takimoto, Deca Pants for Washing Bedridden Drip, Feb. 22, 1994, machine translation (Year: 1994).*
(Continued)

*Primary Examiner* — Nicholas J. Weiss
*Assistant Examiner* — Brandon W. Levy

(57) ABSTRACT

Pants (diaper) for urine or feces capable of disposing of urine or feces several times in a sanitary condition are disclosed. The pants include a front side, a back side, and a connection side configured to connect the front side to the back side. The back side has a hip section corresponding to a hip of a user, a first expansion section and a hip support are sequentially disposed on an internal surface of the hip section, the hip support is lifted according as the first expansion section expands to rise the hip of the user, a space for collecting the urine or the feces is formed between the hip section and the connection side in response to the lifting of the hip.

8 Claims, 9 Drawing Sheets

(58) Field of Classification Search
CPC .......... A61F 13/49413; A61F 13/49011; A61F 13/51104; A41B 9/12
See application file for complete search history.

(56) References Cited

FOREIGN PATENT DOCUMENTS

| | | | |
|---|---|---|---|
| JP | 06013817 U | | 2/1994 |
| JP | H0613817 U | * | 7/1994 |
| JP | 2001129010 A | * | 5/2001 |
| JP | 4004701 B2 | | 8/2001 |
| JP | 2001224616 A | | 8/2001 |
| JP | 2008119172 A | | 5/2008 |
| KR | 10-2009-0109160 A | | 10/2009 |
| KR | 20090109160 A | * | 10/2009 |
| KR | 10-2010-0036663 A | | 4/2010 |
| WO | 2011143972 A1 | | 11/2011 |

OTHER PUBLICATIONS

Nomoto, Diaper, Connection Hose, and Gear for Automatically Treating Excretion, May 15, 2001, machine translation (Year: 2001).*
Yun, Apparatus for Disposing Excrement from Patient, Oct. 20, 2009, machine translation (Year: 2009).*
International Search Report issued from PCT International Application No. PCT/KR2019/006635 issued on Jan. 3, 2020.
Written Opinion issued from PCT International Application No. PCT/KR2019/006635 issued on Jan. 3, 2020.

* cited by examiner

PANTS FOR URINE OR FECES AND METHOD OF DISPOSING OF URINE AND FECES

CROSS-REFERENCE TO RELATED APPLICATIONS

This application is a continuation of PCT International Application No. PCT/KR2019/006635, which was filed on Jun. 3, 2019, and which claims priority from Korean Patent Application No. 10-2019-0039154 filed on Apr. 3, 2019, and Korean Patent Application No. 10-2019-0059408 filed on May 21, 2019. The disclosure of the above patent applications are incorporated herein by reference in their entirety.

TECHNICAL FIELD

The present disclosure relates to pants for urine or feces and method of disposing of urine and feces.

BACKGROUND ART

Most of patients or old men in a nursing hospital can't move very well. Hence, family member or caregiver disposes of urine or feces of the patient while the patient is lying abed.

Particularly, the family member or the caregiver takes off a disposal diaper from the patient when the patient relieves oneself, and then he puts the patient on new diaper. This diaper exchanging process is performed several times a day.

The caregiver exchanges the diaper of the patient because the family member can't care the patient during the daytime, but it is difficult to exchange the diaper at a proper time due to lack of the caregiver. Accordingly, sanitary condition of the patient may not be good.

Additionally, since a diaper for urine and a diaper for feces exist separately, a good many diapers are used a day. As a result, environmental pollution may occur according as many diapers are dumped.

SUMMARY

To solve problem of the conventional technique, the disclosure is to provide pants (diaper) for urine or feces capable of disposing of urine or feces several times in a sanitary condition.

A pants for urine or feces according to one embodiment of the disclosure includes a front side; a back side; and a connection side configured to connect the front side to the back side. Here, the back side has a hip section corresponding to a hip of a user, a first expansion section and a hip support are sequentially disposed on an internal surface of the hip section, the hip support is lifted according as the first expansion section expands to rise the hip of the user, a space for collecting the urine or the feces is formed between the hip section and the connection side in response to the lifting of the hip, and touch of the feces and a skin of the user is minimized.

A pants for urine or feces according to another embodiment of the disclosure includes a front side; a backside; and a connection side configured to connect the front side to the back side. Here, the back side has a hip section corresponding to a hip of a user, at least one hip support is formed in an inner space of the hip section or over an internal surface of the hip section, the hip of the user rises while the hip support is lifted, a space for collecting the urine or the feces is formed between the hip section and the connection side depending on rising of the hip, and touch of the feces and a skin of the user is minimized.

A pants for urine or feces according to still another embodiment of the disclosure includes a front side; a back side; and a connection side configured to connect the front side to the back side. Here, the back side has a hip section corresponding to a hip of a user, a space for collecting the urine or the feces is formed between the hip section and the connection side in response to lifting of the hip, wash water is spurred through a cleaning pipe connected to the back side when the urine or the feces is collected in the space, and the collected urine or feces and contaminated water by the spurring of the wash water are outputted outside through a discharge pipe.

A method of disposing of urine or feces according to one embodiment of the disclosure includes forming a space for collecting the urine or the feces by expanding a part of the pants; spurring wash water to an anus when the urine or the feces is collected in the space; and collecting contaminated water in accordance with washing of the anus by the wash water or the urine or the feces outside the pants. Here, the part of the pants is lifted by injection of air, and a hip of a user rises when the part of the pants is lifted.

Pants (diaper) for urine or feces according to one embodiment of the disclosure may dispose of urine or feces several times and be reused after it is cleaned, and so environmental pollution may reduce.

In the pants for urine or feces, a space for collecting urine or feces is generated according as a hip is lifted, and thus a phenomenon that the urine or the feces in the space is contacted with his skin may be minimized.

BRIEF DESCRIPTION OF DRAWINGS

Example embodiments of the present disclosure will become more apparent by describing in detail example embodiments of the present disclosure with reference to the accompanying drawings, in which.

DETAILED DESCRIPTION

In the present specification, an expression used in the singular encompasses the expression of the plural, unless it has a clearly different meaning in the context. In the present specification, terms such as "comprising" or "including," etc., should not be interpreted as meaning that all of the elements or operations are necessarily included. That is, some of the elements or operations may not be included, while other additional elements or operations may be further included. Also, terms such as "unit," "module," etc., as used in the present specification may refer to a part for processing at least one function or action and may be implemented as hardware, software, or a combination of hardware and software.

The disclosure relates to a diaper for old man or patient (user), specifically a diaper for nursing hospital, and the diaper may dispose of urine or feces several times. Accordingly, it releases inconvenience of exchanging frequently the diaper and urine or feces may be easily disposed of.

In one embodiment, the diaper of the disclosure may make a space for collecting urine or feces when user's urine or feces is sensed, remove immediately urine or feces collected in the space and clean a hip of the user on which the feces is stained. This diaper may be reused after washed.

Specially, the space is formed to minimize contact of urine or feces in the space and the user's skin, and so it is hygienic.

Most of patients or old men in the nursing hospital can't move very well, and thus they relieve themselves while they are lying abed. As a result, family member or caregiver exchanges a disposable diaper several times a day, wherein the disposable diaper may contaminate environment Additionally, since a diaper for urine and a diaper for feces exist separately, the diaper for urine and the diaper for feces should be changed apart. The diaper of the patient is not smoothly exchanged due to lack of the caregiver, and so sanitary condition of the patient may not be good.

To solve this problem, the disclosure provides a diaper capable of disposing of urine or feces several times in a sanitary condition.

Hereinafter, various embodiments of the disclosure will be described in detail with reference to accompanying drawings. It is assumed that patient uses the diaper, for the purpose of convenience of description.

Figure 1:
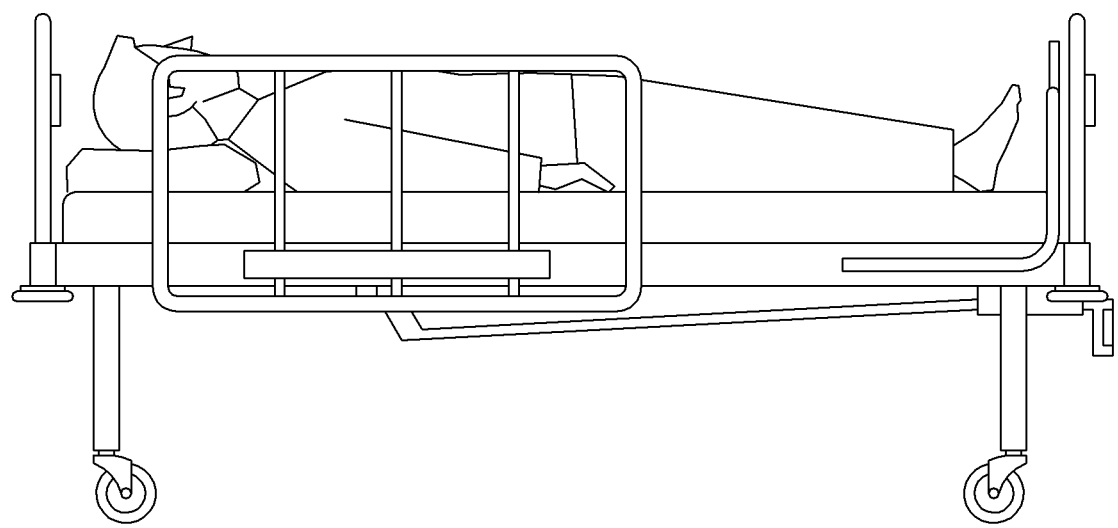
FIG. 1 is a view illustrating patient lying on a bed.
Figure 2:
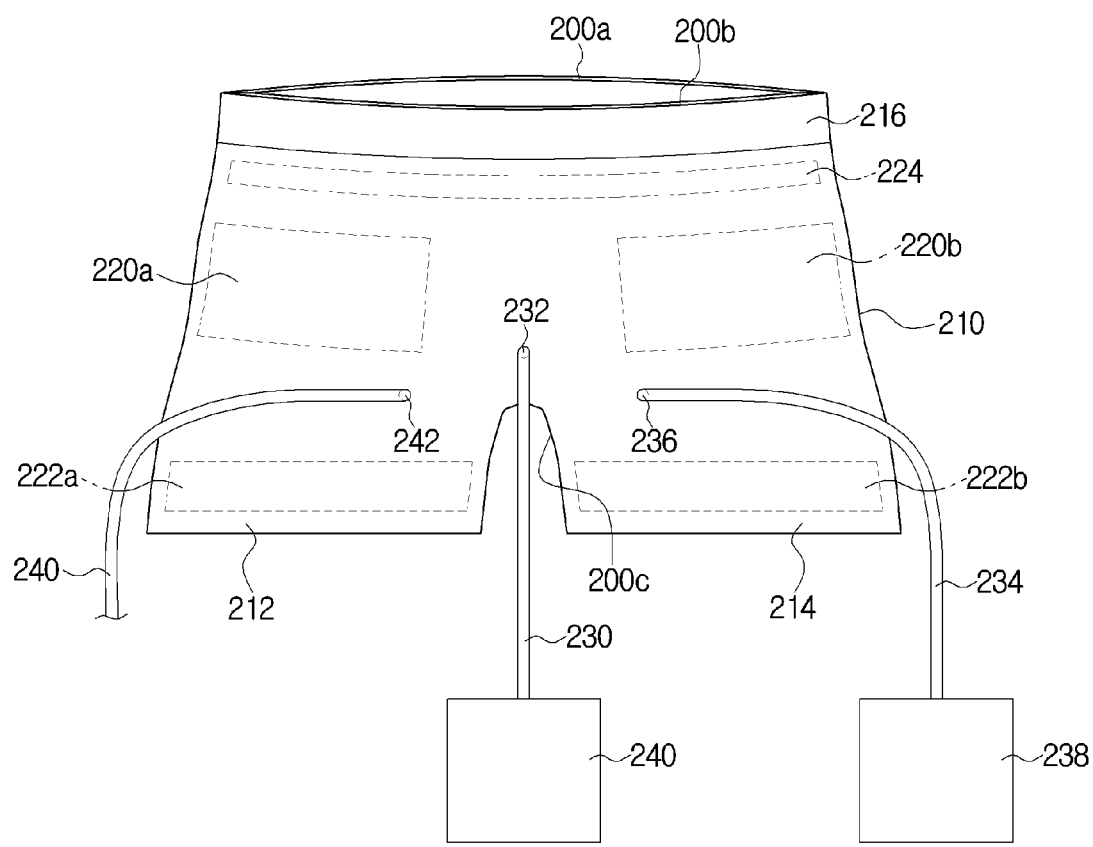
FIG. 2 is a view illustrating a diaper according to an embodiment of the disclosure.
Figure 3A:
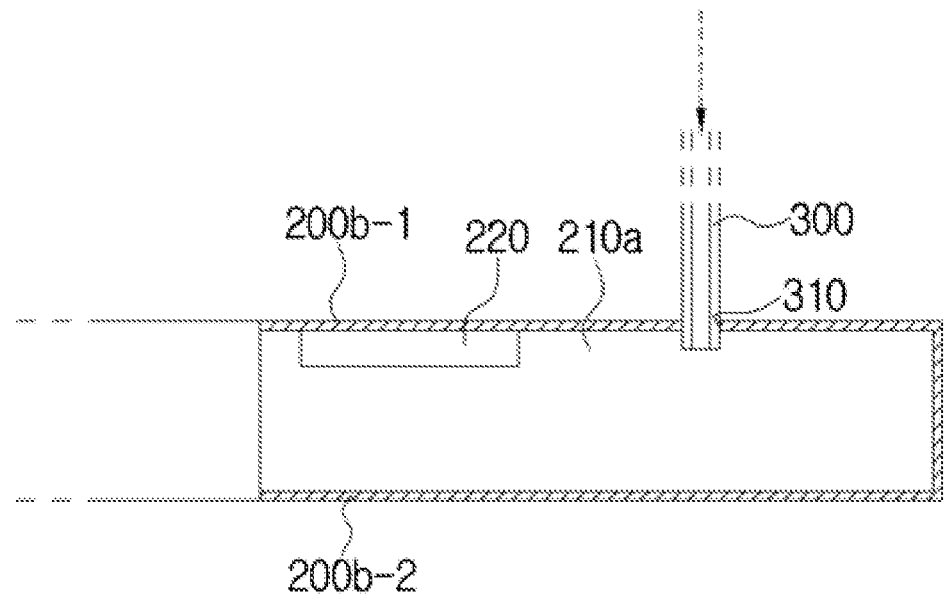
FIG. 3A, FIG. 3B, and FIG. 4 are views illustrating a process of making a space for collecting urine or feces in the diaper according to an embodiment of the disclosure.
Figure 3B:
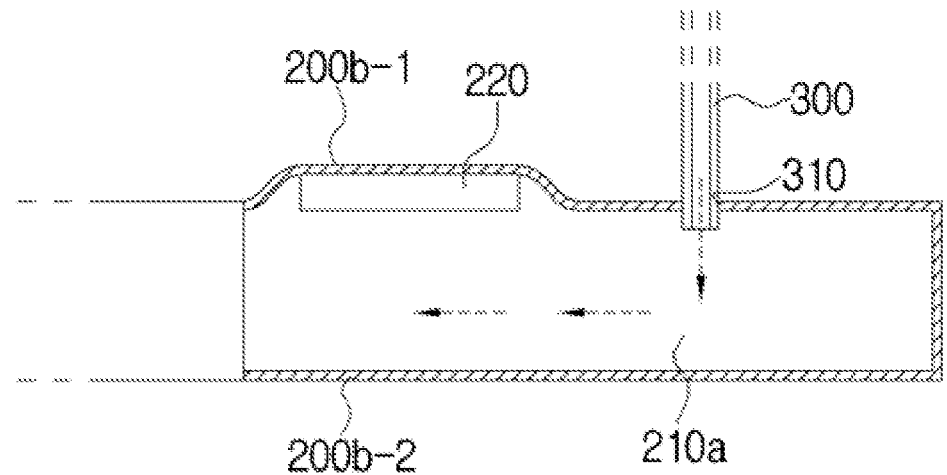
Figure 4:
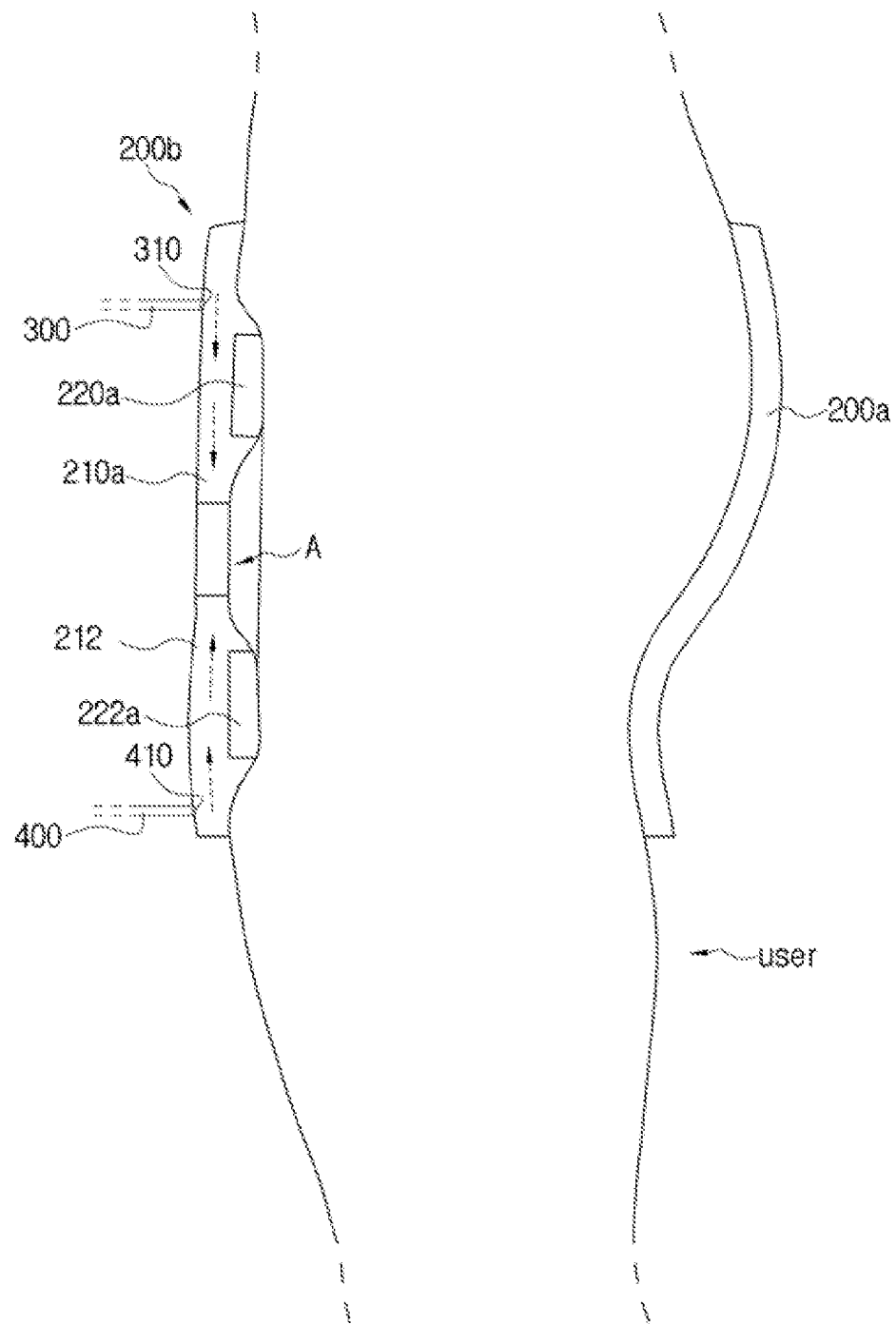
Figure 5A:
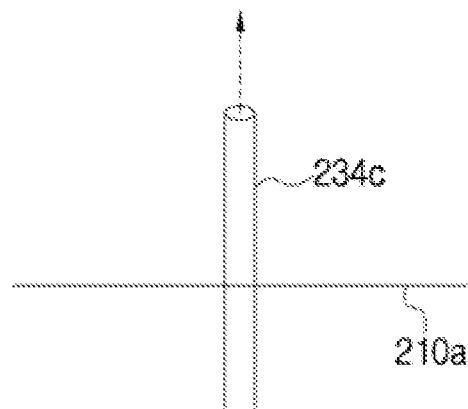
FIG. 5A and FIG. 5B are views illustrating a cleaning structure according to an embodiment of the disclosure.
Figure 5B:
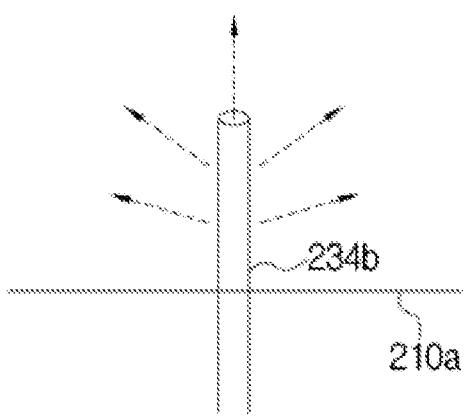

FIG. 1 is a view illustrating patient lying on a bed, and FIG. 2 is a view illustrating a diaper according to an embodiment of the disclosure. FIG. 3A, FIG. 3B, and FIG. 4 are views illustrating a process of making a space for collecting urine or feces in the diaper according to an embodiment of the disclosure, and FIG. 5A and FIG. 5B are views illustrating a cleaning structure according to an embodiment of the disclosure.

The diaper of the present embodiment is for example pants (bottom wear) which patient lying on a bed puts on, and it may dispose of urine or feces several times. Here, the diaper may be used without limitation of usage age, sex etc., and it may be referred to as pants for urine or feces in view of disposing of urine or feces. That is, the diaper is not limited as a diaper for old man, patient or baby and involves every pants capable of disposing of urine or feces.

In FIG. 2, the diaper of the present embodiment includes a front side 200a, a back side 200b and a connection side 200c (bottom part) for connecting the front side 200a to the back side 200b.

The diaper may be worn like a trouser, or is attached type like the diaper for baby. For example, open and close type Velcro or a zipper (locking device) may be formed on left or right of the front side 200a, which is not shown in FIG. 2.

Of course, the locking device may be formed on the back side 200b. However, it is efficient that the locking device is formed on the front side 200a because many elements are formed on the back side 200b as described below.

The back side 200b includes a hip section 210, a first thigh section 212 and a second thigh section 214. Here, the hip section 200b may have hip supports 220a and 220b for supporting left hip and right hip.

The hip supports 220a and 220b support left or right hips and lifts the hip while the user relieves himself (urinates or evacuates), and they are for example pads.

In one embodiment, the hip supports 220a and 220b may have the structure shown in FIG. 3A and FIG. 3B. Particularly, the hip support 220 may be formed on an internal surface 200b-1 of the back side 200b in a space between the internal surface 200b-1 and an outer surface 200b-2 of the back side 200b. Here, the internal surface 200b-1 may mean a part contacted with the hip of patient, and the outer surface 200b-2 may indicate a part touched with a bed.

An air injection pipe 300 may be combined with the internal surface 200b-1 or the outer surface 200b-2 through a connection section 310.

The hip support 220 is lifted as shown in FIG. 3B when an air injection section (not shown) injects air into the space 210a between the internal surface 200b-1 and the outer surface 200b-2 through the air injection pipe 300 as shown in FIG. 3A. As a result, left hip and right hip are lifted by the hip supports 220a and 220b, and so a space A having shape of a bowl may be formed by the hip section 210 and the connection side 200c as shown in FIG. 4. The space A for collecting urine or feces may be formed by the hip section 210, the connection side 200c and thigh sections 212 and 214 corresponding to a thigh support 222a as shown in FIG. 4, when thigh is lifted by the thigh support 222a as follows.

The space A is a space for collecting urine or feces, and urine or feces in the space A is not nearly contacted with a skin of patient because the hip is lifted by the hip supports 220a and 220b. That is, contact of the skin of patient and the feces may be minimized, and so it is hygienic.

In above description, the space A is formed by injecting the air into the space 210a between the internal surface 200b-1 and the outer surface 200b-2. However, methods of forming the space A may be variously modified as long as the space A is formed by lifting the left hip and the right hip. For example, the hip supports 220a and 220b may be lifted by using a mechanical driving.

In one embodiment, a first thigh support 222a may be formed on the first thigh section 212, and a second thigh support 222b may be formed on the second thigh section 214.

The thigh support 222a or 222b may be formed on an internal surface of the thigh section 212 or 214 in a space between the internal surface and an outer surface of the thigh section 212 or 214 as shown in FIG. 4, and it may be lifted by an air injected through an air injection pipe 400 and a connection section 410. As a result, left thigh or right thigh may be also lifted by the thigh supports 222a and 222b.

In this case, the space A having shape of bowl may be formed well as shown in FIG. 4. Furthermore, urine or feces and contaminated water due to cleaning may not be leaked outside because the thigh sections 212 and 214 of the back side 200b are closed to the thigh of patient. As a result, the bed or patient may not get dirty.

In an embodiment, a waist support 224 may be further formed at vicinity of a waist on the back side 200b.

The waist support 224 may also formed on an internal surface of the back side 200b and be lifted by an air injected through an air injection pipe (not shown). As a result, the waist support 224 closes to the waist of patient, and thus urine or feces and contaminated water may not be leaked outside.

A discharge pipe 230, at least one cleaning pipe 234 and a dry pipe 240 may be formed on the back side 200b.

One terminal of the discharge pipe 230 may be connected to a collection section 250, the other terminal of the discharge pipe 230 may be connected to the back side 200b through a connection section 232, and the discharge pipe 230 may inhale urine or feces and the contaminated water. Here, the discharge pipe 230 is removable from the back side 200b through the connection section 232.

In an embodiment, the discharge pipe 230 may correspond to the space A for collecting urine or feces. Accordingly, urine or feces and the contaminated water in the space A may be collected to the collection section 250 through the discharge pipe 230.

On the other hand, the diaper of patient is exchanged while the patient lies on, and thus a hole may be formed on a part of the bed, and the discharge pipe 230 may be connected to the collection section 250 through the hole of the bed. Of course, the discharge pipe 230 may be extended outside on a top side of the bed without forming the hole on the bed.

The collection section 250 is not limited as long as it collects urine or feces and the contaminated water through inhalation of urine or feces and the contaminated water, and it may include an inhalation means (not shown).

One terminal of the cleaning pipe 234 may be connected to a wash water section 238, the other terminal of the cleaning pipe 234 may be connected to the back side 200b through corresponding connection section 236, and the cleaning pipe 234 is removable.

In an embodiment, the cleaning pipe 234 may be formed outside the space A of the back side 200b. This is because the cleaning pipe 234 should not be blocked by urine or feces.

However, since the cleaning pipe 234 should be used for cleaning bowel, it may be disposed toward an anus.

For example, the cleaning pipe 234 may be disposed toward the anus in a left direction or a right direction of the anus, and it may swing depending on spurt water pressure.

In an embodiment, the cleaning pipe 234c may have a structure for emitting straightly wash water as shown in FIG. 5A or the cleaning pipe 234b may have plural emitting holes so that the wash water spreads out as shown in FIG. 5B. Here, the cleaning pipe 234 may be flat on the back side 200b or be projected from the back side 200b as shown in FIG. 5A and FIG. 5B.

However, the cleaning pipe 234 may be normally flat on the back side 200b and be projected from the back side 200b while the user relieves himself.

The wash water section 238 may be a tank for storing the wash water and may function as a pump to output the wash water through the cleaning pipe 234. For another example, the wash water section 238 may be directly connected to a water pipe, and the cleaning pipe 234 may be removable from the wash water section 238.

One terminal of the dry pipe 240 may be connected to a dry section (not shown), the other terminal of the dry pipe 240 is connected to the back side 200b through the connection section 242, and the dry pipe 240 may be removable from the back side 200b.

The dry section may dry a hip cleaned by the wash water by outputting wind through the dry pipe 240.

Briefly, the diaper of the disclosure may make the space A for collecting urine or feces by using the hip supports 220a and 220b and the thigh supports 222a and 222b, clean the anus by using the wash water while the user relieves himself, collect urine, feces and the contaminated water in accordance with the cleaning in the collection section 250, and dry the hip or the anus wet by the wash water by using the wind through the dry pipe 240.

Accordingly, it is not necessary to exchange the diaper though patient relieves himself several times a day and the user may reuse after washing the diaper though he uses continuously the diaper all day or for days. As a result, it is not necessary to exchange frequently the diaper of patient, and so family member or caregiver may make less an effort and environment pollution may reduce.

The diaper of the disclosure may further include an elasticity section 216 for tightening a waist and a sensor (not shown) for sensing urine or feces through moisture and gas generated when the user relieves himself, which is not described above.

The elasticity section 216 may reduce tightening of patient by the diaper when the diaper is expanded by injection of the air. Another elasticity section may be formed on the thigh section 214 of the diaper.

The sensor may be disposed in an internal space of the diaper or formed on an internal surface of the diaper. That is, location of the sensor is not limited as long as the sensor can sense urine or feces. However, it is efficient that the sensor is formed below the hip. This is for sensing immediately gas, etc. outputted from an anus.

Moreover, multiple embossed projection patterns, a crease, etc. may be formed on an upper part of the diaper, and thus touch of the internal surface of the diaper and a skin of patient may be minimized and the air may be naturally circulated.

Furthermore, a stopper may be adhered to the connection section 236 connected to the cleaning pipe 234. This is for blocking a hole of the connection section 236 when the cleaning pipe 234 is separated from the diaper.

Additionally, a massage function may be added on the upper part (corresponding to the waist) of the diaper. The massage may be provided to the waist if an operation of lifting or downing the hip and the thigh of patient is repeated depending on the injection of the air.

Hereinafter, a process of disposing of urine or feces in the diaper of the disclosure will be described. It is assumed that the patient lies on the bed.

The diaper is worn to the patient and then the discharge pipe 230, the cleaning pipe 234 and the dry pipe 240 may be connected to the diaper. Of course, the discharge pipe 230, the cleaning pipe 234 and the dry pipe 240 may be connected to the diaper before the diaper is worn.

Subsequently, the sensor senses emission of urine or feces through moisture or gas.

Then, the hip supports 220a and 220b and the thigh supports 222a and 222b are lifted depending on the injection of the air when the urine or feces is sensed. As a result, the hip and the thigh of patient rises and the space A having the shape of bowl may be formed by the hip section 210 and the connection side 200c. Here, urine or feces is collected in the space A, and so a phenomenon that urine or feces is touched with the skin of the patient is minimized.

On the other hand, the waist support 224 may be lifted together when the hip supports 220a and 220b and the thigh supports 222a and 222b are lifted.

Subsequently, the wash water may be outputted to the anus through the cleaning pipe 234 when it is determined that the emission of urine or feces is completed.

Then, a dry wind may be outputted through the dry pipe 240 to dry the anus wet by the wash water, when output of the wash water is completed.

Subsequently, urine or feces and contaminated water by the wash water are collected to the collection section 250 through the discharge pipe 230. This collecting process may be performed before drying or be performed with drying.

The hip supports 220a and 220b, the thigh supports 222a and 222b and the waist support 224 are returned to an original position, when the collecting is completed. That is, lifted hip supports 220a and 220b, lifted thigh supports 222a and 222b and lifted waist support 224 may be downed.

Subsequently, urine or feces and the contaminated water collected by the collection section 250 may be dumped.

Figure 6A:
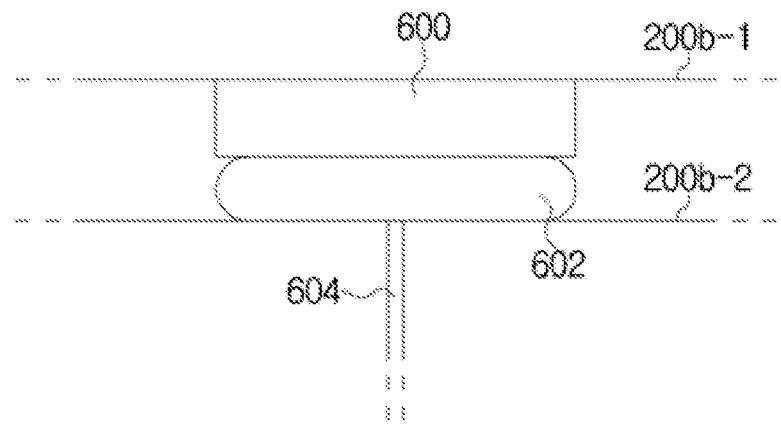
FIG. 6A and FIG. 6B are views illustrating schematically a part of a diaper according to another embodiment of the disclosure.
Figure 6B:
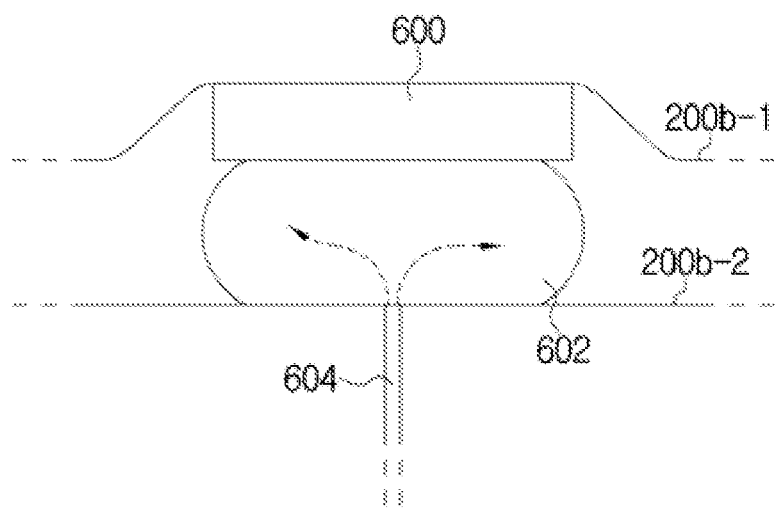

FIG. 6A and FIG. 6B are a view illustrating schematically a part of a diaper according to another embodiment of the disclosure.

Referring to FIG. 6A, a hip support 600 and an expansion section 602 (for example, balloon) may be laminated in a space between an internal surface 200b-1 and an outer surface 200b-2 of a back side of the diaper. That is, unlike only the hip support exists in the space between the internal surface 200b-1 and the outer surface 200b-2, in the present embodiment, the hip support 600 and the expansion section 602 may exist in the space between the internal surface 200b-1 and the outer surface 200b-2.

In the event that air is injected to the expansion section 602 through an air injection pipe 604, the expansion section 602 is expanded as shown in FIG. 6B, thereby lifting the hip support 600. As a result, the hip of patient may rise.

A thigh support and another expansion section may be laminated in the space between the internal surface 200b-1 and the outer surface 200b-2 of a back side of the diaper in view of the thigh, which is not shown in FIG. 6A and FIG. 6B. The thigh support may be lifted according as air is injected to the expansion section.

A space where urine or feces is collected is formed when the hip support 600 and the thigh supports rise. Any further description concerning the space will be omitted because it is described above.

Figure 7:
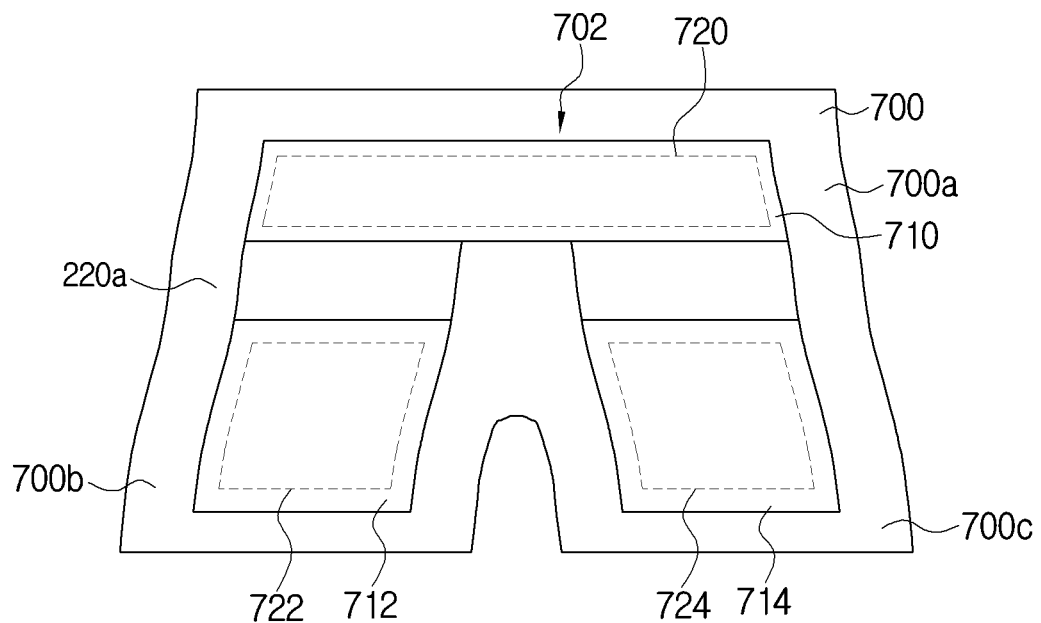
FIG. 7 is a view illustrating schematically a part of a diaper according to still another embodiment of the disclosure.
Figure 8:
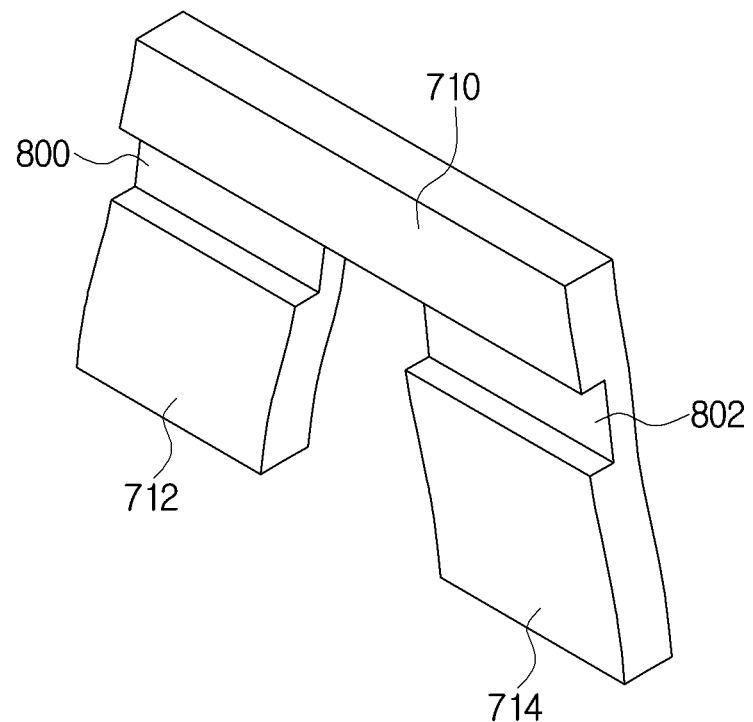
FIG. 8 is a view illustrating a supporting member according to an embodiment of the disclosure.
Figure 9A:
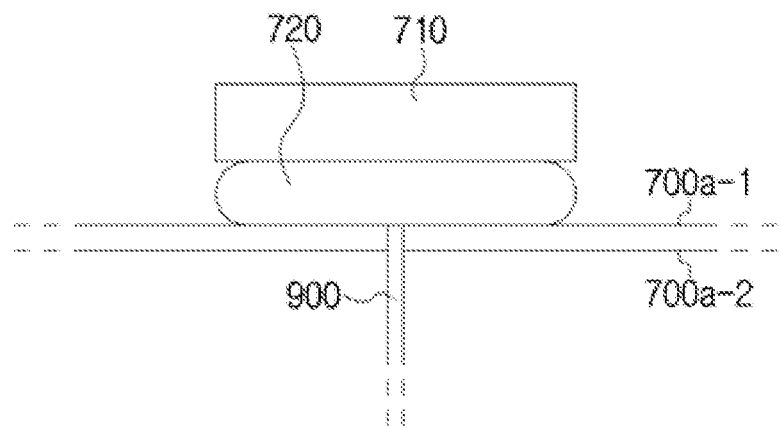
FIG. 9A and FIG. 9B are views illustrating an operation of a hip support according to an embodiment of the disclosure.
Figure 9B:
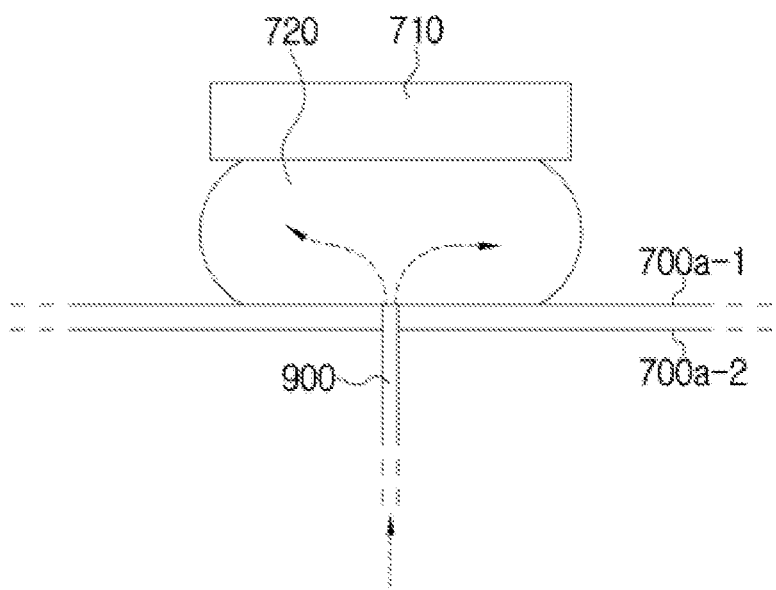
Figure 10A:
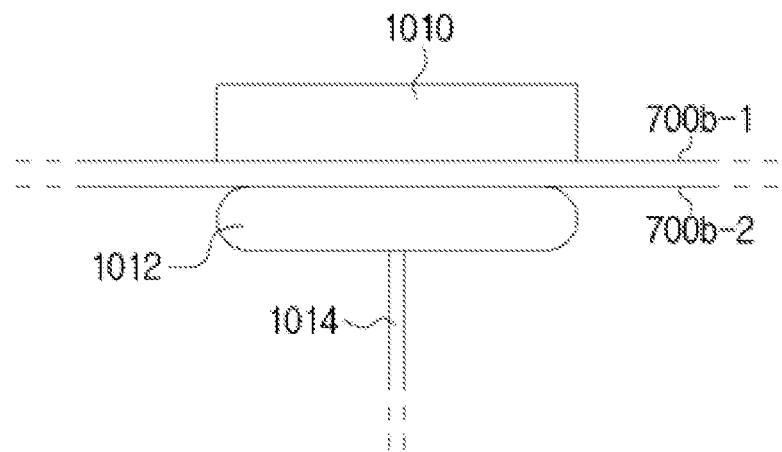
FIG. 10A and FIG. 10B are views illustrating an operation of a thigh support according to an embodiment of the disclosure.
Figure 10B:
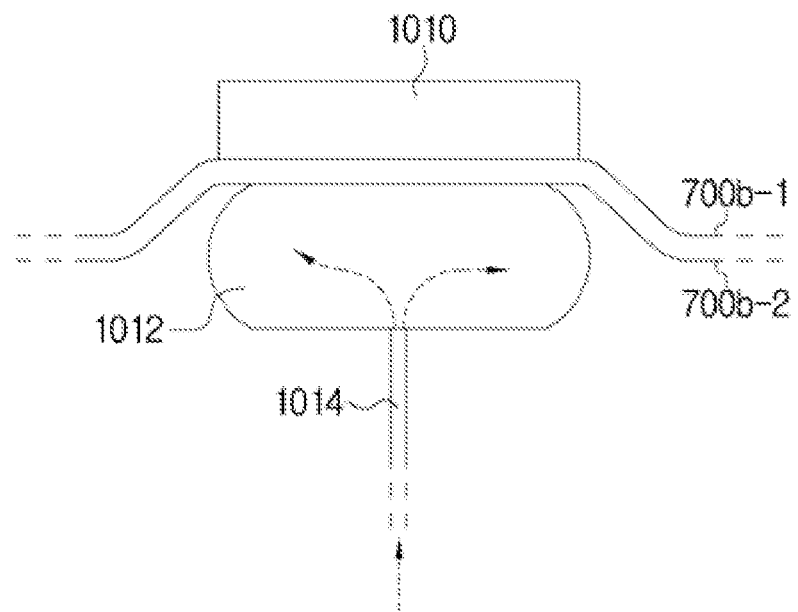
Figure 11:
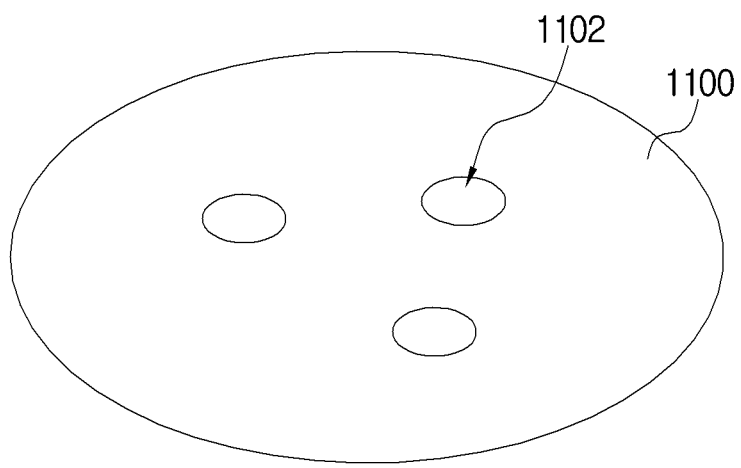
FIG. 11 is a view illustrating a pipe structure according to an embodiment of the disclosure.

FIG. 7 is a view illustrating schematically a part of a diaper according to still another embodiment of the disclosure, and FIG. 8 is a view illustrating a supporting member according to an embodiment of the disclosure. FIG. 9A and FIG. 9B are a view illustrating an operation of a hip support according to an embodiment of the disclosure, and FIG. 10A and FIG. 10B are a view illustrating an operation of a thigh support according to an embodiment of the disclosure. FIG. 11 is a view illustrating a pipe structure according to one embodiment of the disclosure. However, FIG. 7 shows only the back side of the diaper, for the purpose of convenience of description.

In FIG. 7, the supporting member 702 may locate on a hip section 700a of an internal surface of a back side 700 of the diaper, and expansion section 720, 722 and 724 may be disposed between the internal surface and the supporting member 702. In another embodiment, the expansion section 722 and 724 may locate below an outer surface of the back side 700 of the diaper.

In FIG. 8, the supporting member 702 may include a hip support 710, a first thigh support 712, a second thigh support 714, a first connection section 800 for connecting the hip support 710 to the first thigh support 712 and a second connection section 802 for connecting the hip support 710 to the second thigh support 714. That is, the hip support 710 and the thigh supports 712 and 714 have integral structure. Of course, the hip support 710 and the thigh supports 712 and 714 may be independent members and the connection sections 800 and 802 don't exist.

In an embodiment, the hip support 710 and the thigh supports 712 and 714 may have height greater than the connection section 800 or 802, and a cleaning pipe, etc. may be crossly disposed over the connection members 800 and 802.

Referring to FIG. 9A and FIG. 9B, an expansion section 720 located between the hip support 710 and an internal surface 700a-1 of the hip section 700a expands when air is injected to the expansion section 720 through an air injection pipe 900. As a result, the hip support 710 is lifted, and thus the hip rises. In an embodiment, an expansion section 720 may be disposed an outer surface 700a-2 of the hip section.

In FIG. 10A and FIG. 10B, the thigh support 1010 is disposed on an internal surface 700b-1 of a thigh section of the back side 700 of the diaper, and an expansion section 1012 is disposed below an outer surface 700b-2 of the thigh section. In the event that air is injected into the expansion section 1012 through an air injection pipe 1014, the thigh support 1010 is lifted, and thus the thigh rises.

Of course, the expansion section and the thigh support 1010 may be sequentially disposed on the internal surface 700b-1. On the other hand, since the thigh section rises in FIG. 10A and FIG. 10B, it is efficient to move urine, etc. in the direction of a discharge pipe.

Briefly, a space for collecting urine or feces may be naturally formed according as the hip support 710 and the thigh supports 1010 rise.

The discharge pipe, a cleaning pipe and a dry pipe are not mentioned in above embodiments, they are the same as in FIG. 1 to FIG. 6B or similar to those in FIG. 1 to FIG. 6B, and thus any further description concerning the same or similar elements will be omitted.

The discharge pipe, the cleaning pipe and the dry pipe may be directly combined with the diaper like above embodiments, or they may be combined with a pipe structure 1100 formed on an internal surface of the diaper as shown in FIG. 11.

For example, the pipe structure 1100 may be formed of hard plastic, and it may include at least one hole 1102 through which the discharge pipe, the cleaning pipe or the dry pipe is combined. That is, the discharge pipe, the cleaning pipe or the dry pipe may be combined with the pipe structure 1100 without being directly combined with the diaper.

Of course, the pipe structure 1100 may have a structure for connecting an outer pipe extended toward the diaper to an inner pipe located inside the diaper.

That is, combination structure and combination method may be variously modified as long as the pipe structure 1100 combines the discharge pipe, the cleaning pipe or the dry pipe.

Components in the embodiments described above can be easily understood from the perspective of processes. That is, each component can also be understood as an individual process. Likewise, processes in the embodiments described above can be easily understood from the perspective of components.

The invention claimed is:

1. A pants for urine or feces comprising:
a front side;
a back side; and
a connection side configured to connect the front side to the back side,
wherein the back side has a hip section corresponding to a hip of a user, a first expansion section and a hip support pad are sequentially disposed on an outer surface of the hip section or on an internal surface of the hip section, the hip support pad is lifted when the first expansion section expands by injection of air, wherein the back side includes a thigh section corresponding to a thigh of the user, a thigh support pad is disposed in an inner space of the thigh section or on an internal surface of the thigh section, a second expansion section is disposed below an outer surface of the thigh section, the thigh support pad is lifted when the second expansion section expands by injection of air, and wherein a space for collecting the urine or the feces is formed by the hip support pad, the connection side and the thigh support pad.

2. The pants of claim 1, further comprising a connection section for connecting the hip support pad to the thigh support pad, wherein the connection section is thinner than the hip support pad and the thigh support pad, wherein the hip support, the thigh support and the connection section are formed in one body structure.

3. The pants of claim 2, further comprising a cleaning pipe for emitting washing water, wherein one terminal of the cleaning pipe is connected to a wash water section and the other terminal of the cleaning pipe is connected to the back side, wherein the cleaning pipe is removable, is projected from the back side, and has plural emitting holes to spread the washing water.

4. The pants of claim 1, wherein a waist support is further formed on an upper part of the back side, and wherein the waist support is lifted by injection of air, and a part corresponding to the waist support of the back side is configured to close to a skin of the user to prevent leakage of the urine or the feces and contaminated water depending on the lifting of the waist support.

5. The pants of claim 1, wherein an elasticity section is formed on an upper part of the pants, an embossed projection pattern or a crease is formed on the upper part so that air is circulated in the pants.

6. A pants for urine or feces comprising:
a front side;
a backside; and
a connection side configured to connect the front side to the back side,
wherein the back side has a hip section corresponding to a hip of a user and thigh sections corresponding to thighs of the user, at least one hip support pad is formed in an inner space of the hip section or over an internal surface of the hip section, thigh support pads are disposed in an inner space of the thigh sections or on an internal surface of the thigh sections,
wherein the hip support pad and thigh support part are configured to lift the hips and thighs of the user, and a space for collecting the urine or the feces is formed in the hip section, the thigh sections and the connection side depending on rising of the hip and the thighs.

7. The pants of claim 6, wherein the hip support pad is formed on an internal surface adjacent to skin of the user in the inner space of the hip section, a first expansion section is sequentially disposed in the inner space of the hip section, and the first expansion section expands when air is injected into the expansion section to rise the hip section.

8. The pants of claim 7,
wherein a second expansion section is sequentially disposed below the thigh support pads, the thigh support pads are lifted when the second expansion section expands by injection of air, and the thigh sections are configured to close to the thighs of the user in response to the lifting of the thigh support pads to prevent leakage of the urine or the feces collected in the space.

* * * * *